United States Patent [19]

Hsu et al.

[11] Patent Number: 5,064,845
[45] Date of Patent: Nov. 12, 1991

[54] FUNGICIDAL COMPOSITIONS AND METHODS OF USE

[75] Inventors: Adam C. Hsu, Lansdale; Daniel L. Loughner, Huntingdon Valley, both of Pa.

[73] Assignee: Rohm and Haas Company, Independence Mall West, Pa.

[21] Appl. No.: 631,803

[22] Filed: Dec. 20, 1990

Related U.S. Application Data

[63] Continuation-in-part of Ser. No. 530,770, May 29, 1990, which is a continuation-in-part of Ser. No. 370,373, Jun. 22, 1989, abandoned.

[51] Int. Cl.$^5$ .................... A01N 43/82; A01N 43/653
[52] U.S. Cl. .................................. 514/364; 514/340; 514/384; 546/276; 546/277; 548/144; 548/263.2
[58] Field of Search ................... 514/364, 384, 340

[56] References Cited

FOREIGN PATENT DOCUMENTS 4602071 4/1986 World Int. Prop. O. .......... 514/384

Primary Examiner—Robert Gerstl
Attorney, Agent, or Firm—Polly E. Ramstad

[57] ABSTRACT

This invention relates to the use of iodopropargyl compounds invention have the structure

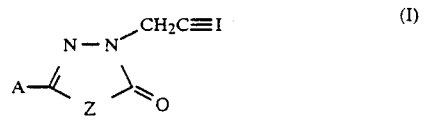

wherein
A is hydrogen, alkyl, cycloalkyl, alkenyl, alkynyl, phenyl, phenylalkyl, naphthyl or heterocyclyl; and
Z is oxygen (O) or N—R;

wherein R is hydrogen, alkyl, cycloalkyl, phenyl, or phenylalkyl as agricultural fungicides and to agricultural fungicidal compositions containing the iodopropargyl compounds.

36 Claims, No Drawings

FUNGICIDAL COMPOSITIONS AND METHODS OF USE

This application is a continuation-in-part of Ser. No. 530,770, filed May 29, 1990, which is a continuation-in-part of Ser. No. 370,373, filed June 22, 1989 abandoned, both of which are incorporated herein by reference.

This invention relates to the use of iodopropargyl compounds as agricultural fungicides and to agricultural fungicidal compositions containing the iodopropargyl compounds.

Every year fungus diseases cause great damage to crops and thus appreciably lower their yield. Current fungicides do not have the combination of a good spectrum of activity, good plant tolerance and simple and inexpensive synthesis which is desired in compounds used to control these fungal diseases. Thus there remains a need for new fungicides which have one or more of these properties.

The compounds which are active in the method of the present invention have the structure

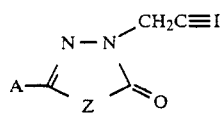

wherein
A is hydrogen, alkyl, cycloalkyl, alkenyl, alkynyl, phenyl, phenylalkyl, naphthyl or heterocyclyl; and
Z is oxygen (O) or N-R; wherein R is hydrogen, alkyl, cycloalkyl, phenyl, or phenylalkyl.

Alkyl means straight and branched alkyl groups, for example $(C_1-C_{18})$alkyl such as methyl, ethyl, n-propyl, isopropyl, n-butyl, isobutyl, t-butyl, n-hexyl, n-heptyl, n-octyl, n-dodecyl or n-heptadecyl. An alkyl portion of any one of the substituents listed above for A or Z is optionally substituted by one to five halogens to form groups such as trifluoromethyl or 1,1,1,2,2-pentafluoroethyl. Cycloalkyl is, for example, cyclohexyl and includes cycloalkyl optionally substituted by $(C_1-C_4)$alkyl or halo. Phenyl is optionally substituted with one to three substituents such as $(C_1-C_4)$alkyl, halogen, $(C_1-C_4)$alkoxy, halo$(C_1-C_4)$alkyl, halo$(C_1-C_4)$alkoxy, nitro, cyano, carboxy, $(C_1-C_4)$alkoxycarbonyl, $(C_1-C_4)$alkylthio, $(C_1-C_4)$alkylsulfonyl or $(C_1-C_4)$alkylsulfinyl. Heterocyclyl is a five or six-membered aromatic heterocycle, for example thienyl, pyridyl or furyl such as 2-thienyl, 2-furyl, 2-pyridyl or 3-pyridyl.

In an embodiment of the invention, compounds which are useful in the method of the invention have the formula

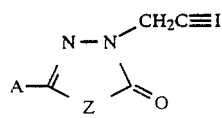

wherein
A is hydrogen, $(C_1-C_{18})$alkyl, $(C_3-C_8)$cycloalkyl, $(C_3-C_6)$alkenyl, $(C_3-C_6)$alkynyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, phenyl($C_1-C_6$)alkyl, naphthyl, thienyl, furyl or pyridyl; and
Z is oxygen (O) or N-R;
wherein R is hydrogen, $(C_1-C_{12})$alkyl, $(C_3-C_6)$cycloalkyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, or phenyl$(C_1-C_6)$alkyl are used to control fungal disease in plants.

In a preferred embodiment of the method of the invention are compounds of the formula

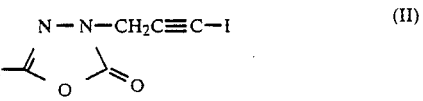

wherein A is $(C_1-C_{18})$alkyl, $(C_3-C_8)$cycloalkyl, phenyl optionally substituted with one to three substituents selected from halo, nitro, $(C_1-C_6)$alkyl, halo$(C_1-C_6)$alkyl, halo$(C_1-C_6)$alkoxy and $(C_1-C_6)$ alkoxy, phenyl($C_1-C_6$)alkyl, naphthyl, thienyl, furyl or pyridyl.

More preferred are compounds wherein A is phenyl, halophenyl, $(C_1-C_4)$alkylphenyl, nitrophenyl, halo$(C_1-C_4)$alkylphenyl or di$(C_1-C_4)$alkoxyphenyl.

Even more preferred are compounds wherein A is phenyl, fluorophenyl, chlorophenyl, methylphenyl, nitrophenyl, trifluoromethylphenyl or dimethoxyphenyl.

Most preferred are compounds wherein A is phenyl, 2-fluorophenyl, 2-chlorophenyl, 3-chlorophenyl, 4-chlorophenyl, 2-methylphenyl, 3-methylphenyl, 2-nitrophenyl, 4-trifluoromethylphenyl or 2,5-dimethoxyphenyl.

In another preferred embodiment of the method of the invention are compounds of the formula

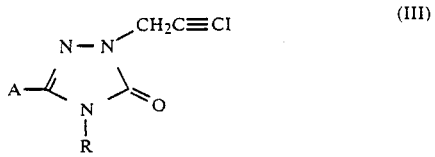

wherein A is hydrogen or $(C_1-C_4)$alkyl and R is phenyl optionally substituted by one to three substituents selected from halo, $(C_1-C_4)$alkyl, $(C_1-C_4)$alkoxy or nitro.

More preferred are compounds wherein A is hydrogen or t-butyl and R phenyl optionally substituted by one to three substituents selected from halo, $(C_1-C_4)$alkyl, $(C_1-C_4)$alkoxy or nitro.

Even more preferred are compounds wherein R is phenyl, fluorophenyl, chlorophenyl, methylphenyl, ethylphenyl, nitrophenyl, dichlorophenyl or dimethylphenyl.

Most preferred are compounds wherein when A is hydrogen, R is 2-fluorophenyl, 3-chlorophenyl, 2-methylphenyl, 3-methylphenyl, 4-methylphenyl, 3-ethylphenyl, 4-ethylphenyl, 2,4-dichlorophenyl, 3,5-dichlorophenyl, 3,5-dimethylphenyl or 2,4-dimethylphenyl; and when A is t-butyl, R is phenyl, 4-chlorophenyl ore 3-fluorophenyl.

In yet another preferred embodiment of the method of the invention are compounds having the formula

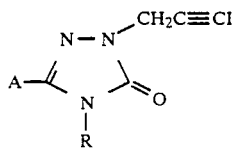

(III)

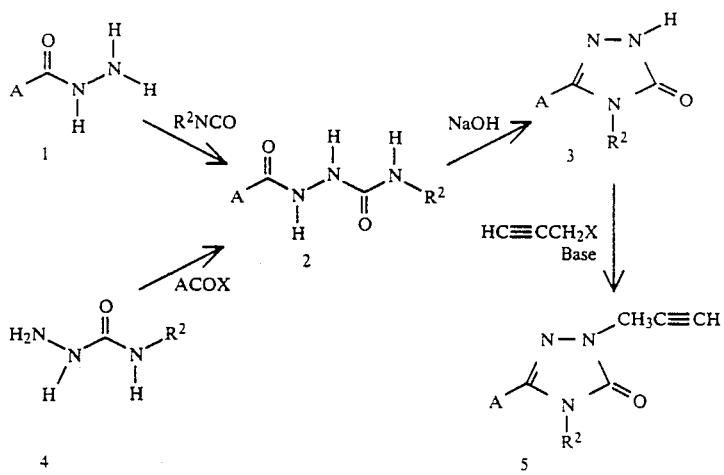

wherein A is hydrogen, $(C_1-C_4)$alkyl or phenyl optionally substituted by halo or $(C_1-C_4)$alkyl and R is $(C_1-C_{16})$alkyl or $(C_3-C_6)$cycloalkyl.

More preferred are compounds wherein when A is hydrogen, R is $(C_3-C_6)$cycloalkyl; when A is $(C_1-C_4)$alkyl, R is $(C_1-C_4)$alkyl or $(C_3-C_6)$cycloalkyl or A is fluorophenyl, chlorophenyl or methylphenyl and R is $(C_1-C_4)$alkyl.

Most preferred are compounds wherein A is hydrogen and R is cyclohexyl; A is methyl and R is n-hexyl or cyclohexyl; and A is 2-flourophenyl, 3-fluorophenyl, 4-fluorophenyl, 2-chlorophenyl, 4-chlorophenyl, 2-methylphenyl or 4-methylphenyl and R is ethyl.

The compounds used in the instant invention can be prepared by a variety of methods.

One suitable method comprises reacting a compound of the formula (IV)

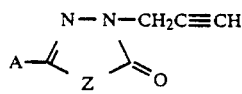

with an iodinating agent.

Suitable iodinating agents include, for example, iodine, an iodine-amino compound such as morpholine-iodine complex, and N-iodosuccinimide ("NIS"), the latter being the most preferred.

When an iodine or iodo-amino compound is used, base should also be used, preferably sodium or potassium hydroxide, and solvent such as methanol, ethanol, and aqueous ethanol should also be used.

When NIS is used, a catalyst such as, for example, silver nitrate, or the like, should be used in presence of solvent such as acetone, methyl ethyl ketone, tetrahydrofuran, and the like.

Reaction times of about 20 minutes to about 24 hours have been utilized successfully with reaction temperatures of about 0° C. to about 25° C.

The compounds of formula IV when Z is N-R can be prepared by a variety of methods.

One suitable method comprises using an acyl semicarbazide 2, which is prepared either from a hydrazide 1 or a semicarbazide 4.

When starting from a hydrazide, the hydrazide is reacted with an isocyanate in an inert organic solvent such as ethyl ether, glyme, tetrahydrofuran, ethyl acetate, benzene, or toluene or mixtures thereof at a temperature of from about 0° C. to about 100° C., preferably from about 15° C. to about 50° C.

When starting from the semicarbazide, the semicarbazide is reacted with an acylating agent such as an acid chloride or anhydride in the presence of a base in an inert or substantially inert solvent or mixture of solvents to yield the desired acyl semicarbazide.

Suitable solvents for use in the above processes include water; alcohols such as methanol, ethanol, and isopropanol; hydrocarbons such as toluene, xylene, hexane and heptane; glyme; tetrahydrofuran; acetonitrile; pyridine; or haloalkanes such as methylene chloride or mixtures of these solvents.

Preferred solvents are water, toluene, methylene chloride or a mixture of these solvents.

The resulting compound 3 is then alkylated with propargyl bromide or propargyl chloride in the presence of base to yield compound 5.

Examples of bases for use in the above processes include tertiary amines such as triethylamine; pyridine; potassium carbonate; sodium carbonate; sodium bicarbonate; sodium hydroxide; or potassium hydroxide. Preferred bases are sodium hydroxide, potassium hydroxide or triethylamine.

The acyl semicarbazide is cyclized by heating the compound in a basic solution such as 5% sodium hydroxide or potassium hydroxide at a temperature between about 0° C. and about 150° C. preferably from about 50° C. to about 120° C.

The compounds of formula IV wherein Z is oxygen can be prepared similarly by reacting the hydrazide 2 with a chloroformate in place of the isocyanate and obtaining directly the desired oxadiazolinone.

The following examples further illustrate this invention but are not intended to limit it in any way. In Tables I and II, typical compounds useful in the method of the invention are listed with their melting points. The proton NMR data are listed in Table III for those compounds for which no melting point is supplied. Structures were confirmed by NMR and in some cases by IR and/or elemental analysis. Specific illustrative preparations of the compounds are described after Table III.

TABLE I

N—N—CH₂C≡C—I / A / O / O

| Cmpd No. | A | A substituent | mp °C. |
|---|---|---|---|
| 1. | CH₃ | | 90–96 |
| 2. | CH₂CH₂CH₃ | | 42–46 |
| 3. | (CH₂)₃CH₃ | | oil |
| 4. | C(CH₃)₃ | | 90–93 |
| 5. | (CH₂)₆CH₃ | | Oil |
| 6. | (CH₂)₁₆CH₃ | | 41–46 |
| 7. | phenyl | | 137–139 |
| 8. | phenyl | 2-F | 139–142 |
| 9. | phenyl | 3-F | 127–129 |
| 10. | phenyl | 4-F | 127–129 |
| 11. | phenyl | 2-Cl | 104–107 |
| 12. | phenyl | 3-Cl | 124–126 |
| 13. | phenyl | 4-Cl | 151–152 |
| 14. | phenyl | 3-Br | 127–129 |
| 15. | phenyl | 4-Br | 159–162 |
| 16. | phenyl | 2-CH₃ | 152–154 |
| 17. | phenyl | 3-CH₃ | 114–115 |
| 18. | phenyl | 4-CH₃ | 174–175 |
| 19. | phenyl | 2-NO₂ | 116–120 |
| 20. | phenyl | 3-NO₂ | 99.5–102 |
| 21. | phenyl | 4-NO₂ | 176–178 |
| 22. | phenyl | 4-CF₃ | 144–147 |
| 23. | phenyl | 2-OCH₃ | 115–117 |
| 24. | phenyl | 3-OCH₃ | 128–130 |
| 25. | phenyl | 4-OCH₃ | 171–173 |
| 26. | phenyl | 2-OCH₂CH₃ | 138–142 |
| 27. | phenyl | 3-OCH₂CH₃ | 129–132 |
| 28. | phenyl | 2-Cl, 4-NO₂ | 161–166 |
| 29. | phenyl | 2,5-Cl₂ | 121–123 |
| 30. | phenyl | 3,5-(OCH₃)₂ | 161–165 |
| 31. | phenyl | 2,5-(OCH₃)₂ | 144–147 |
| 32. | phenyl | 4-phenyl | 183–186 |
| 33. | phenyl | 3,4,5-(OCH₃)₃ | 135–137 |
| 34. | 2-thienyl | | 149–151 |
| 35. | 2-furyl | | 140–142 |
| 36. | 1-naphthyl | | 167–169 |

TABLE II

N—N—CH₂C≡CI / A / N—R / O

| NO. | A | R | mp °C. |
|---|---|---|---|
| 37. | H | CH₂CH₃ | Oil |
| 38. | H | CH₂CH₂CH₂CH₃ | 66–70 |
| 39. | H | (CH₂)₅CH₃ | Oil |
| 40. | H | Cyclohexyl | 118–122 |
| 41. | H | (CH₂)₇CH₃ | Oil |
| 42. | H | (CH₂)₁₁CH₃ | 50–52 |
| 43. | H | phenyl | 192–193 |
| 44. | H | 2-F-phenyl | 115–120 |
| 45. | H | 3-F-phenyl | 172–175 |
| 46. | H | 4-F-phenyl | 124–127 |
| 47. | H | 2-Cl-phenyl | 139–140 |
| 48. | H | 3-Cl-phenyl | 112–115 |
| 49. | H | 4-Cl-phenyl | 147–149 |
| 50. | H | 3-Br-phenyl | 105–110 |
| 51. | H | 4-Br-phenyl | 175–177 |
| 52. | H | 2-CH₃-phenyl | 132–134 |
| 53. | H | 3-CH₃-phenyl | 153–156 |
| 54. | H | 4-CH₃-phenyl | 165–170 |
| 55. | H | 3-CH₂CH₃-phenyl | 82–87 |
| 56. | H | 4-CH₂CH₃-phenyl | 129–132 |
| 57. | H | 4-CH₃O-phenyl | 117–120 |
| 58. | H | 4-NO₂-phenyl | 165–166 |

TABLE II-continued

N—N—CH₂C≡CI / A / N—R / O

| NO. | A | R | mp °C. |
|---|---|---|---|
| 59. | H | 2,4-Cl₂-phenyl | 148–151 |
| 60. | H | 3,4-Cl₂-phenyl | 160–161 |
| 61. | H | 3,5-Cl₂-phenyl | 101–105 |
| 62. | H | 2,6-Cl₂-phenyl | 115–120 |
| 63. | H | 3,5-(CH₃)₂-phenyl | 80–85 |
| 64. | H | 2,4-(CH₃)₂-phenyl | 119–124 |
| 65. | H | Benzyl | 119–124 |
| 66. | CH₃ | CH₂CH₃ | Oil |
| 67. | CH₃ | (CH₂)₅CH₃ | Oil |
| 68. | CH₃ | Cyclohexyl | 103–106 |
| 69. | CH₃ | phenyl | 179–182 |
| 70. | CH₃ | 4-Cl-phenyl | 129–131 |
| 71. | CH₃ | 4-CH₃-phenyl | 166–170 |
| 72. | CH₃ | 4-CH₃O-phenyl | 200–203 |
| 73. | CH₃ | Benzyl | 170–172 |
| 74. | CH₂CH₂CH₃ | CH₂CH₃ | 89–93 |
| 75. | CH₂CH₂CH₃ | phenyl | 106–112 |
| 76. | CH₂CH₂CH₃ | 4-Cl-phenyl | 50–56 |
| 77. | CH₂CH₂CH₃ | 2-CH₃O-phenyl | Oil |
| 78. | CH₂CH₂CH₃ | 3-CH₃O-phenyl | 109–112 |
| 79. | CH₂CH₂CH₃ | 4-CH₃O-phenyl | Oil |
| 80. | (CH₂)₃CH₃ | CH₂CH₃ | Oil |
| 81. | C(CH₃)₃ | CH₃ | Oil |
| 82. | C(CH₃)₃ | CH₂CH₃ | Oil |
| 83. | C(CH₃)₃ | phenyl | 170–174 |
| 84. | C(CH₃)₃ | 3-CH₃O-phenyl | 168–170 |
| 85. | C(CH₃)₃ | 4-Cl-phenyl | 168–171 |
| 86. | C(CH₃)₃ | 3-F-phenyl | 151–160 |
| 87. | phenyl | CH₂CH₃ | 144–148 |
| 88. | 2-F-phenyl | CH₃ | 121–126 |
| 89. | 2-F-phenyl | CH₂CH₃ | 121–124 |
| 90. | 3-F-phenyl | CH₃ | 124–129 |
| 91. | 3-F-phenyl | CH₂CH₃ | 104–107 |
| 92. | 4-F-phenyl | CH₃ | 122–125 |
| 93. | 4-F-phenyl | CH₂CH₃ | 108–111 |
| 94. | 2-Cl-phenyl | CH₂CH₃ | 86–89 |
| 95. | 3-Cl-phenyl | CH₃ | 78–82 |
| 96. | 3-Cl-phenyl | CH₂CH₃ | — |
| 97. | 4-Cl-phenyl | CH₃ | 148–152 |
| 98. | 4-Cl-phenyl | CH₂CH₃ | 115–120 |
| 99. | 4-Cl-phenyl | phenyl | 193–195 |
| 100. | 4-Cl-phenyl | 4-Cl-phenyl | 171–177 |
| 101. | 4-Cl-phenyl | 4-CH₃-phenyl | 179–183 |
| 102. | 3-Br-phenyl | CH₃ | 89–94 |
| 103. | 3-Br-phenyl | CH₂CH₃ | — |
| 104. | 4-Br-phenyl | CH₃ | 145–150 |
| 105. | 4-Br-phenyl | CH₂CH₃ | 125–126 |
| 106. | 2-CH₃-phenyl | CH₂CH₃ | Oil |
| 107. | 3-CH₃-phenyl | CH₂CH₃ | Oil |
| 108. | 4-CH₃-phenyl | CH₂CH₃ | 141–145 |
| 109. | 4-CH₃-phenyl | (CH₂)₃CH₃ | — |
| 110. | 4-CH₃-phenyl | CH(CH₃)₂ | — |
| 111. | 3-NO₂-phenyl | CH₂CH₃ | 153–158 |
| 112. | 4-NO₂-phenyl | CH₂CH₃ | 184–187 |
| 113. | 2-OCH₃-phenyl | CH₂CH₃ | 127–130 |
| 114. | 3-OCH₃-phenyl | CH₂CH₃ | — |
| 115. | 4-OCH₃-phenyl | CH₂CH₃ | Oil |
| 116. | 3-OCH₂CH₃-phenyl | CH₂CH₃ | — |
| 117. | 1-naphthyl | CH₂CH₃ | 148–152 |
| 118. | 2-naphthyl | CH₂CH₃ | 63–70 |
| 119. | 2-thienyl | CH₂CH₃ | 134–136 |
| 120. | 3-pyridyl | CH₂CH₃ | 129–131 |

TABLE III

| Cmpd No. | NMR DATA (200 MHz, delta scale in ppm, Tetramethylsilane (TMS) standard, CDCl₃ as solvent) |
|---|---|
| 2. | 4.60 (2H, s, CH₂), 2.55 (2H, t, CH₂), 1.74 (2H, m CH₂), 1.02 (3H, t, CH₃) |
| 3. | 4.60 (2H, s, CH₂), 2.60 (2H, t, CH₂), 1.70 (2H, m, CH₂), |

TABLE III-continued

NMR DATA
Cmpd (200 MHz, delta scale in ppm, Tetramethylsilane
No. (TMS) standard, CDCl₃ as solvent)

| Cmpd No. | NMR Data |
|---|---|
| | 1.42 (2H, m, CH₂), 0.95 (3H, t, CH₃) |
| 5. | 4.62 (2H, s, CH₂), 2.58 (2H, t, CH₂), 1.70 (2H, m, CH₂), 1.32 (12H, m, 4CH₂), 0.90 (3H, t, CH₃) |
| 37. | 7.42 (1H, s), 4.64 (2H, s, CH₂), 3.70 (2H, q, CH₂), 1.34 (3H, t, CH₃) |
| 39. | 7.45 (1H, s, olefinic H), 4.74 (2H, s, CH₂), 3.64 (2H, t, CH₂), 1.72 (2H, m, CH₂), 1.35 (6H, m, 3CH₂), 0.90 (3H, t, CH₃) |
| 41. | 7.44 (1H, s, olefinic H), 4.72 (2H, s, CH₂), 3.62 (2H, t, CH₂), 1.72 (2H, m, CH₂), 1.30 (10H, m, 5CH₂), 0.90 (3H, t, CH₃) |
| 66. | 4.68 (2H, s, CH₂), 3.72 (2H, q, CH₂), 2.26 (3H, s, CH₃), 1.30 (3H, t, CH₃) |
| 67. | 4.70 (2H, s, CH₂), 3.60 (2H, t, CH₂), 2.26 (3H, s, CH₃), 1.64 (6H, m, CH₂), 1.34 (6H, m, 3CH₂), 0.91 (3H, t, CH₃) |
| 77. | 7.55-7.02 (4H, m, arom.H), 4.78 (2H, s, CH₂), 3.86 (3H, s, CH₃), 2.32 (2H, q, CH₂), 1.60 (2H, m, CH₂), 0.90 (3H, t, CH₃) |
| 79. | 7.22 (4H, q, arom.H), 4.76 (2H, s, CH₂), 3.85 (3H, s, CH₃), 2.40 (2H, t, CH₂), 1.58 (2H, m, CH₂), 0.90 (3H, t, CH₃) |
| 80. | 4.82 (2H, s, CH₂), 3.70 (2H, q, CH₂), 2.40 (2H, t, CH₂), 1.66 (2H, m, CH₂), 1.38 (5H, m), 0.98 (3H, t, CH₃) |
| 81. | 4.72 (2H, s, CH₂), 3.42 (3H, s, CH₃), 1.40 (9H, s, 3CH₃) |
| 82. | 4.70 (2H, s, CH₂), 3.88 (2H, q, CH₂), 1.38 (12H, m, 4CH₃) |
| 96. | 7.60 (4H, m, arom.H), 4.81 (2H, s, CH₂), 3.85 2H, q, CH₂), 1.32 (3H, t, CH₃) |
| 103. | 7.80 to 7.40 (4H, m, arom.H), 4.80 (2H, CH₂), 3.84 (2H, q, CH₂), 1.30 (3H, t, CH₃) |
| 106. | 7.35 (4H, m, arom.H), 4.80 (2H, s, CH₂), 3.56 (2H, q, CH₂), 2.29 (3H, s, CH₃) 1.12 (3H, t, CH₃) |
| 107. | 7.34 (4H, m, arom.H), 4.78 (2H, s, CH₂), 3.80 (2H, q, CH₂), 2.40 (3H, s, CH₃), 1.25 (3H, t, CH₃) |
| 109. | 7.40 (4H, q, arom.H), 4.78 (2H, s, CH₂), 3.80 2H, t, CH₂), 2.44 (3H, s, CH₃), 1.62 (2H, m, CH₂), 1.30 (2H, m, CH₂), 0.85 (3H, t, CH₃) |
| 110. | 7.38 (4h, q, arom.H), 4.75 (2H, s, CH₂), 4.26 (1H, m, CH), 2.45 (3H, s, CH₃), 1.55 (6H, d, 2-CH₃) 1.55 (6H, d, 2-CH₃) |
| 114. | 7.50 to 7.00 (4H, m, arom.H), 4.80 (2H, s, CH₂), 3.85 (4H, m, CH₃ & CH₂), 1.30 (3H, t, CH₃) |
| 115. | 7.20 (4H, aromatic H), 4.75 (2H, s, CH₂) 3.84 (3H, s, CH₃), 3.75 (2H, q, CH₂) 1.28 (3H, t, CH₃) |
| 116. | 7.50 to 7.00 (4H, m, arom.H), 4.80 (2H, s, CH₂), 4.10 (2H, q, CH₂), 3.84 (2H, q, CH₂), 1.46 (3H, t, CH₃), 1.26 (3H, t, CH₃) |

EXPERIMENTAL

Example 13

2-(4-Chlorophenyl)-4-(3iodopropargyl)-1,3,4-oxadiazolin-5-one

To a suspension of 4-chlorobenzhydrazide (8.53 grams (g), 0.05 mole) in methylene chloride (100 milliliters (ml)), was dropwise added trichloromethyl chloroformate (5.94 g, 0.03 mole). After addition, the reaction mixture was heated to reflux for 2 hours. The reaction was cooled down to room temperature and poured into a mixture of water (500 ml) and hexane (200 ml) and stirred for 10 to 20 min. The resultant precipitate was collected by suction-filtration and was washed with hexane to give a solid product. The product was dried in air at room temperature overnight yielding 5.5 g (60% yield) of 2-(4-chlorophenyl)-1,3,4-oxadiazolin-5one as a solid, m.p. 225°-227° C. NMR and IR spectra showed the desired structure. Without further purification, this product was subjected to the next step.

To the suspension of 2-(4-chlorophenyl)-1,3,4-oxadiazolin-5-one (2 g, 0.01 mole) in acetone (50 ml) was added potassium carbonate (2 g, 0.015 mole), followed by propargyl bromide (1.6 g of 80% in toluene, 0.0106 mole) and the mixture was stirred under nitrogen for 3 hours. The reaction mixture was cooled down to room temperature. The suspension was filtered by suction-filtration and the solid was washed with acetone. The filtrate was concentrated to about 10 ml and was poured into water (200 ml). The resultant precipitate was collected by suction-filtration and washed with water and hexane to yield 0.85 g (36% yield), after drying in air, of 2-(4-chlorophenyl)-4-propargyl-1,3,4-oxadiazolin-5-one as a solid, m.p. 125°-127° C. NMR and IR spectra showed the desired structure. Without further purification, this compound was subjected to the next step.

To the suspension of 2-(4-chlorophenyl)-4-propargyl-1,3,4-oxadiazolin-5-one (0.6 g, 0.00256 mole) in acetone (20 ml) with magnetic stirring at room temperature was added N-iodosuccinimide (0.6 g, 0.00266 mole), followed by silver nitrate (0.040 g, 0.00024 mole). The reaction mixture was stirred at room temperature for one hour. The suspension was filtered gravitationally and the solid was rinsed with acetone. The filtrate was poured into water (300 ml). The resultant precipitate was collected by suction-filtration and air-dried to give 0.8 g (92% yield), of 2-(4-chlorophenyl)-4-(3-iodopropargyl)-1,3,4-oxadiazolin-5-one as a solid, m.p.151°-152° C. The proton NMR spectrum was consistent with the desired structure.

Compounds 1-12 and 13-36 were prepared using essentially the same procedure.

Example 98

1-(3-Iodopropargyl)-3-(4-chlorophenyl)-4-ethyl-1,2,4-triazolin-5-one

To a suspension of 4-chlorobenzhydrazide (98.5 g, 0.05 mole) in tetrahydrofuran (100 ml) at room temperature ethylisocyanate (4.2 g, 0.05 mole) was added slowly with magnetic stirring. The reaction was slightly exothermic and the reaction mixture turned to a thick paste. Stirring was continued an additional 30 min after which the solid was collected by suction-filtration and washed with a small amount of tetrahydrofuran and dried to provide 11.6 g (96.6% yield), of 1-(4-chlorobenzoyl)-4-ethyl semicarbazide as a white solid, m.p. 242°-243° C. The above semicarbazide (10 g, 0.0414 mole) was dissolved in 1N sodium hydroxide solution (100 ml) and was refluxed with stirring for 16 hr. The solution was cooled down to about 10° C. by an ice bath and was neutralized by conc. hydrogen chloride until pH 2. The resultant white solid was collected by suction-filtration and washed with water to give 8.65 g (93.5% yield) of 3-(4-chlorophenyl)-4-ethyl-1,2,4-triazolin-5-one as a white solid. m.p. 190°-197° C. A proton NMR spectrum was consistent with the desired structure.

To the solution of 3-(4-chlorophenyl)-4-ethyl-1,2,4-triazolin-5-one (2.23 g, 0.01 mole) in dry acetone (40 ml) was added, at room temperature, potassium carbonate (1.67 g, 0.0012 mole) followed by propargyl bromide (1.8 g of 80% in toluene, 0.012 mole). The reaction mixture was then refluxed with stirring for 6 hr. The mixture was cooled down to room temperature and solvent was evaporated to give a residue. The product was purified by crystallization from hexane/ether, affording 1.8 g (69.2% yield) of 1-propargyl-3-(4-chlorophenyl)-4-ethyl-1,2,4-triazolin-5-one as a white solid, m.p. 115°-119° C. A proton NMR spectrum was consistent with the desired structure.

To the solution of 1-propargyl-3-(4-chlorophenyl)-4-ethyl-1,2,4-triazolin-5-one (1.0 g, 3.82 mmole) in dry acetone (20 ml) was added N-iodosuccinimide (0.95 g, 4.2 mmole), followed by silver nitrate (50 mg, 0.29 mmole) with magnetic stirring at room temperature. The reaction mixture was stirred for 1 hr. The resultant suspension was filtered and the filtrate was poured into water (250 ml). A yellowish white solid slowly precipitated out and was collected by suction-filtration and washed with water to give 1.12 g (76% yield) of 1-(3-iodopropargyl)-3-(4-chloro-phenyl)-4-ethyl-1,2,4-triazolin-5-one as a light yellow solid. m.p.=115°-120° C. A proton NMR spectrum was consistent with the desired compound.

Compounds 37–97 and 99–120 were prepared following essentially the same procedure.

The present invention provides a method for controlling a broad range of phytopathogenic Phycomycetes and some fungi classified as Deuteromycetes (Fungi Imperfecti), Ascomycetes, and Basidiomycetes. Important genera of the Phycomycetes include Phytophthora, Plasmorpora, Peronospora, and Pseudoperonospora which cause diseases such as potato and tomato late blight, and downy mildews in grapes, squash, melons, broccoli and other cole crops. Basidiomycetes, such as Pellicularia and Puccinia spp. are also controlled by the method of the invention. Species of these genera cause diseases such as rice sheath blight (*Pellicularia filamentosa*) and wheat rusts, (*Puccinia graminis* and *Puccinia recondita*. Ascomycetes, such as Venturia and Erysiphe spp. are controlled by the method of this invention. Species in these genera cause diseases such as apple scab (*Venturia inequalis*) and wheat powdery mildew (*Erysiphe graminis* F. sp. tritici). Plant root and stalk rots caused by Fusarium spp. can also be controlled by the present invention.

Late blights, downy mildews, many root rots and damping-off diseases have been difficult to control due to the lack of effective control methods. Some of the more effective chemical control measures have become ineffective due to the development of resistant fungal strains. The compounds of Formula (I) can be used to control these types of fungi, particularly late blights and downy mildews.

The compounds of the invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, but the effective amount is usually from about 0.5 kilogram (kg) to about 20 kg, preferably from about 1 to about 5 kg of active ingredient per hectare.

As a seed protectant, the amount of toxicant coated on the seed is usually at a dosage rate of about 1 kg to about 5 kg and preferably from about 0.5 to about 2.5 kg per 100 kilograms of seed. As a soil fungicide the chemical can be incorporated in the soil or applied to the surface usually at a rate of 0.5 to about 20 kg and preferably about 1 to about 5 kg per hectare. As a foliar fungicide, the compounds are usually applied to growing plants at a rate of about 0.5 to about 5 and preferably from about 1 to about 2.5 kg per hectare.

The present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers* and *Detergents, McCutcheon's Emulsifiers* and *Detergents/Functional Materials* and *McCutcheon's Functional Materials* all published annually by McCutcheon Division of MC Publishing Company (New Jersey).

In general, the compounds of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulfsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of cyclododecylamine methoxyactate, 45 parts of a synthetic precipitated hydrated silicon dioxide sold under the trademark Hi-Sil ® and 5 parts of sodium lignosulfonate (Marasperse ® N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex ® 7.

Dusts are prepared by mixing the amides and salts and complexes thereof with finely divided inert solids which can be organic or inorganic in nature. Materials useful for this purpose include botanica flours, silicas, silicates, carbonateds and clays. One covenient method of preparing a dust is to dilute a wettable powder with a finely divided carrier. Dust concentrates containing 20% to 80% of the active ingredient are commonly made and are subsequently diluted to 1% to 10% use concentration.

The compounds of the present invention can also be utilized in combination with other fungicides such as:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, terbuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl) alanine methyl ester, D,L-methyl-N-(2,6-dimethylphenyl)-N-chloroacetyl-D,L-2 aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chlorothalonil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and triclazole.

It is particularly advantageous to utilize the present invention in combination with a dithiocarbamate, e.g., mancozeb or maneb, for added control of non-phycomycetes fungi.

The triazolone compositions may be used to prevent or treat a wide variety of infections caused by fungi.

The compounds of the invention were tested for in vitro activity using the following tests.

The organisms employed in the test were:

| PYU | *Pythium ultimum* (Oomycete) |
| PHY | *Phytophthora capsici* (Oomycete) |

-continued

| PIR | *Piricularia oryzae* (Ascomycete) |
| HEL | *Cochliobolus sativus* (Ascomycete) |
| BOC | *Botrytis cinerea* (Ascomycete) |
| FUS | *Fusarium roseum* (Ascomycete) |
| SEP | *Septoria nodorum* (Ascomycete) |
| RHI | *Rhizoctonia solani* (Basidiomycete) |
| XAN | *Xanthomonas campestris* (bacterium) |

METHODS

1. Culture maintenance: Transfers in steps 1 and 2 were done in a laminar flow hood. All 8 fungi and the bacterium used in this test were transferred and maintaned on potato dextrose agar plates each week (2 plates/organism). Organisms were used when they were the following ages: a. 1 week old: PYU, PHY, RHI; b. 2 weeks old: XAN, PIR, BOC, HEL, FUS, SEP, COL, MON, CER, UST, ALT; c. 3 weeks old: PSH, VEN. *Pythium ultimum* and *Phytophthora capsici* were transferred to asparagine-sucrose broth shake cultures (ASB). *Rhizoctonia solani, Fusarium roseum*, and *Xanthomonas campestris* were mainted in yeast extract-dextrose broth (YDB) on a shaker. Culture flasks were inoculated with 6 mycelial plugs each (except for Pythium which was inoculated with only 3 plugs) taken from PDA plates. All liquid shaker cultrues were used after 2 days growth.

2. Inoculum preparation. Conidia and mycelium from PIR, BOC, HEL, SEP, COL, MON, CER, PSH, UST and ALT were lightly scraped off into YDB so that mostly conidia were used as inoculum. The conidial suspension was strained through a double layer of cheesecloth to remove mycelial clumps. One plate produced enough conidia or mycelium to inoculate 100 ml of YDB. XAN broth culture was poured (1 ml culture/100 ml broth) into YDB. PYU, PHY, RHI and FUS cultures were ground up (2-3 5 second bursts in a blender) and all but Pythium and Phytophthora were filtered through a dobule layer of sterile cheesecloth to remove large mycelial clumps. Ten ml of the culture solutions of *R. solani* and *F. roseum* were added to 90 ml of YSB and 10 ml of the *P. capsici* wes added to 90 ml ASB. Two ml of the culture solution of *P. ultimum* is added to 98 ml of ASB. Care was made not to overinoculate (e.g. solutions appeared fairly clear to the eye, yet when held up to light a faint cloudiness was visible) or standards would not behave properly. The inoculum mixtures were placed in microtiter plates using a 12-tipped pipet. 175 $\mu$l (single dose) or 100 $\mu$l (dose-response test) of inoculum broth wes placed in each well of the microtiter plates. The plates with inoculated media were placed in the refrigerator overnight. There were two replications per treatment.

3. Addition of compounds. This operation was carried out in a chemistry hood. Six microtiter plates had 245 microliters of sterile water added to their wells ahead of time. 10 mg a.i. of the compounds were placed in 1 ml 1:1 acetone:methanol. 5 microliters of this solution was pipetted into the microtiter plates containing the sterile water according to the grid. There were 45 compounds and 3 scattered control treatments per plate. There were 2 replicates per treatment. 25 microliters of solution was transferred to the inoculated plates with a 96 well replicator. The replicator was flame sterilized with alcohol, rinsed with sterile water, and blotted on sterile paper towels between each transfer.

The results are reported in Table IV as percent control of each organism tested.

TABLE IV

The Results of In-Vitro Plant Fungicide Tests

| Cmpd | Dose (PPM) | PYU | XAN | PIR | PHY | BOC | HEL | RHI | FUS | SEP |
|---|---|---|---|---|---|---|---|---|---|---|
| 1. | 25 | 100 | 0 | 100 | 100 | 100 | 100 | 100 | 100 | 100 |
| 2. | 25 | 100 | 0 | 100 | 100 | 100 | 100 | 100 | 100 | 100 |
| 3. | 25 | 100 | 0 | 100 | 100 | 100 | 100 | 100 | 100 | 100 |
| 4. | 25 | 100 | 0 | 100 | 100 | 100 | 100 | 100 | 100 | 100 |
| 6. | 25 | 0 | 0 | 0 | 0 | 0 | 0 | 0 | 0 | 0 |
| 7. | 25 | 100 | 0 | 100 | 100 | 90 | 100 | 100 | 100 | 100 |
| 8. | 25 | 95 | 0 | 100 | 100 | 0 | 100 | 95 | 100 | 100 |
| 9. | 25 | 100 | 0 | 100 | 100 | 100 | 100 | 100 | 100 | 100 |
| 10. | 25 | 100 | 0 | 95 | 100 | 100 | 100 | 100 | 100 | 100 |
| 11. | 25 | 100 | 0 | 100 | 100 | 50 | 95 | 100 | 100 | 100 |
| 12. | 25 | 100 | 0 | 100 | 100 | 100 | 100 | 100 | 100 | 100 |
| 13. | 25 | 100 | 0 | 100 | 100 | 100 | 100 | 100 | 100 | 100 |
| 14. | 25 | 100 | 0 | 100 | 100 | 100 | 100 | 100 | 100 | 100 |
| 15. | 25 | 100 | 0 | 100 | 100 | 0 | 100 | 100 | 100 | 100 |
| 16. | 25 | 95 | 0 | 75 | 95 | 0 | 75 | 100 | 100 | 95 |
| 17. | 25 | 100 | 0 | 95 | 95 | 0 | 100 | 90 | 100 | 100 |
| 18. | 25 | 100 | 0 | 75 | 75 | 0 | 90 | 95 | 100 | 95 |
| 19. | 25 | 100 | 0 | 100 | 95 | 90 | 95 | 100 | 100 | 100 |
| 20. | 25 | 50 | 0 | 0 | 100 | 0 | 90 | 0 | 100 | 100 |
| 21. | 25 | 0 | 0 | 0 | 0 | 0 | 75 | 90 | 100 | 0 |
| 22. | 25 | 95 | 0 | 95 | 90 | 50 | 100 | 90 | 100 | 100 |
| 23. | 25 | 100 | 0 | 100 | 100 | 0 | 100 | 100 | 100 | 100 |
| 24. | 25 | 100 | 0 | 100 | 100 | 0 | 100 | 100 | 100 | 100 |
| 25. | 25 | 100 | 0 | 100 | 100 | 0 | 100 | 100 | 100 | 100 |
| 26. | 25 | 100 | 0 | 100 | 95 | 50 | 95 | 50 | 0 | 95 |
| 27. | 25 | 100 | 0 | 100 | 100 | 75 | 100 | 100 | 100 | 100 |
| 28. | 25 | 100 | 0 | 100 | 100 | 90 | 100 | 100 | 100 | 100 |
| 29. | 12 | 0 | 0 | 100 | 100 | 0 | 0 | 50 | 0 | 50 |
| 30. | 25 | 0 | 0 | 0 | 50 | 0 | 50 | 0 | 0 | 0 |
| 31. | 25 | 100 | 0 | 100 | 100 | 0 | 75 | 100 | 0 | 0 |
| 32. | 25 | 100 | 0 | 100 | 100 | 0 | 50 | 75 | 0 | 95 |
| 33. | 25 | 90 | 0 | 75 | 90 | 0 | 0 | 100 | 0 | 0 |
| 34. | 25 | 100 | 0 | 100 | 100 | 100 | 100 | 100 | 100 | 100 |
| 35. | 25 | — | 0 | 100 | 100 | 75 | 100 | 100 | 100 | 100 |
| 36. | 25 | 0 | 0 | 100 | 0 | 0 | 50 | 0 | 0 | 0 |
| 37. | 25 | 100 | 0 | 100 | 100 | 90 | 100 | 100 | 100 | 100 |
| 38. | 25 | 100 | 0 | 100 | 100 | 100 | 100 | 100 | 100 | 100 |
| 39. | 25 | 100 | 0 | 100 | 100 | 100 | 100 | 100 | 100 | 100 |
| 40. | 25 | 100 | 0 | 100 | 100 | 100 | 100 | 100 | 100 | 100 |
| 43. | 25 | 100 | 0 | 95 | 100 | 100 | 95 | 95 | 95 | 95 |
| 44. | 25 | 100 | 50 | 100 | 100 | 100 | 100 | 100 | 100 | 100 |
| 45. | 25 | 100 | 0 | 100 | 100 | 100 | 100 | 100 | 100 | 100 |
| 46. | 25 | 100 | 0 | 100 | 100 | 100 | 100 | 100 | 100 | 100 |
| 47. | 25 | — | — | — | 100 | — | — | 100 | 100 | — |
| 48. | 25 | 100 | 0 | 100 | 100 | 100 | 100 | 100 | 100 | 100 |
| 49. | 25 | 100 | 0 | 100 | 100 | 100 | 100 | 100 | 100 | 100 |
| 50. | 25 | 100 | 0 | 100 | 100 | 100 | 100 | 100 | 100 | 100 |
| 51. | 25 | 100 | 0 | — | 100 | 100 | 75 | 100 | 100 | 100 |
| 53. | 25 | 100 | 0 | 100 | 100 | 100 | 100 | 100 | 100 | 100 |
| 54. | 25 | — | — | — | 100 | — | — | 100 | 100 | — |
| 57. | 25 | 100 | 0 | 100 | 100 | 100 | 100 | 100 | 100 | 100 |
| 58. | 25 | 100 | 0 | — | 100 | 95 | 0 | 90 | 90 | 100 |
| 59. | 25 | 100 | 0 | 100 | 100 | 100 | 100 | 100 | 100 | 100 |
| 60. | 25 | 100 | 0 | 100 | 100 | 100 | 100 | 100 | 100 | 100 |
| 61. | 25 | 100 | 0 | 100 | 100 | 100 | 100 | 100 | 100 | 100 |
| 65. | 25 | 100 | 0 | 100 | 100 | 100 | 100 | 100 | 100 | 100 |
| 66. | 25 | 100 | 0 | 100 | 100 | 0 | 100 | 100 | 0 | 0 |
| 69. | 25 | 100 | 0 | 100 | 100 | 100 | 100 | 100 | 100 | 100 |
| 70. | 25 | 100 | 0 | 100 | 100 | 100 | 100 | 100 | 100 | 100 |
| 74. | 25 | 50 | 0 | 100 | 100 | 0 | 100 | 100 | 90 | 100 |
| 75. | 25 | 100 | 0 | 100 | 100 | 50 | 100 | 100 | 100 | 100 |
| 76. | 25 | 100 | 0 | 100 | 100 | 50 | 100 | 100 | 100 | 100 |
| 80. | 25 | 100 | 0 | 100 | 100 | 100 | 100 | 100 | 100 | 100 |
| 81. | 25 | 100 | 0 | 100 | 100 | 75 | 100 | 100 | 100 | 50 |
| 82. | 25 | 100 | 0 | 100 | 100 | 50 | 100 | 100 | 100 | 50 |
| 83. | 25 | 100 | 0 | 100 | 100 | 90 | 100 | 100 | 100 | 100 |
| 84. | 25 | 100 | 0 | 100 | 100 | 0 | 75 | 100 | 100 | 50 |
| 85. | 25 | 100 | 0 | 100 | 100 | 100 | 75 | 100 | 100 | 100 |
| 86. | 25 | 100 | 0 | 100 | 100 | 0 | 75 | 100 | 100 | 100 |
| 87. | 25 | 100 | 0 | 100 | 100 | 0 | 100 | 100 | 100 | 100 |
| 88. | 25 | 100 | 0 | 100 | 100 | 100 | 100 | 100 | 100 | 100 |
| 89. | 25 | 100 | 0 | 100 | 100 | 0 | 100 | 100 | 100 | 100 |
| 90. | 25 | 100 | 0 | 100 | 100 | 100 | 100 | 100 | 100 | 100 |
| 91. | 25 | 100 | 0 | 95 | 100 | 0 | 75 | 95 | 90 | 50 |
| 92. | 25 | 100 | 0 | 100 | 100 | 100 | 100 | 100 | 100 | 100 |
| 93. | 25 | 100 | 0 | 100 | 100 | 0 | 100 | 100 | 100 | 100 |

TABLE IV-continued

The Results of In-Vitro Plant Fungicide Tests

| Cmpd | Dose (PPM) | PYU | XAN | PIR | PHY | BOC | HEL | RHI | FUS | SEP |
|---|---|---|---|---|---|---|---|---|---|---|
| 94. | 25 | 90 | 0 | 100 | 95 | 0 | 100 | 100 | 100 | — |
| 95. | 25 | 100 | 0 | 100 | 100 | 100 | 100 | 100 | 100 | 100 |
| 96. | 25 | 50 | 0 | 100 | 100 | 0 | 100 | 100 | 90 | 100 |
| 97. | 25 | 100 | 0 | 100 | 100 | 100 | 100 | 100 | 100 | 100 |
| 98. | 25 | 100 | 0 | 100 | 100 | 0 | 95 | 100 | 100 | 100 |
| 99. | 25 | 90 | 0 | 100 | 95 | 0 | 100 | 100 | 100 | — |
| 100. | 25 | 0 | 0 | 90 | 0 | 0 | 0 | 0 | 50 | 0 |
| 101. | 25 | 0 | 0 | 100 | 0 | 0 | 50 | 50 | 100 | 0 |
| 102. | 25 | 100 | 0 | 100 | 100 | 100 | 100 | 100 | 100 | 100 |
| 104. | 25 | 100 | 0 | 100 | 100 | 100 | 100 | 100 | 100 | 100 |
| 105. | 25 | 100 | 0 | 100 | 100 | 0 | 100 | 100 | 100 | 100 |
| 106. | 25 | 100 | 0 | 100 | 100 | 75 | 100 | 100 | 100 | 100 |
| 107. | 25 | 100 | 0 | 100 | 100 | 0 | 100 | 75 | 100 | 100 |
| 108. | 25 | 100 | 0 | 100 | 100 | 0 | 95 | 100 | 100 | 100 |
| 109. | 25 | 50 | 0 | 100 | 50 | 0 | 0 | 0 | 50 | 75 |
| 110. | 25 | 0 | 0 | 0 | 0 | 0 | 0 | 0 | 0 | — |
| 111. | 25 | 0 | 0 | 0 | 0 | 0 | 0 | 0 | 0 | 0 |
| 112. | 25 | 100 | 0 | 100 | 100 | 0 | 100 | 100 | 100 | 100 |
| 113. | 25 | 50 | 0 | 100 | 50 | 0 | 0 | 50 | 0 | 75 |
| 114. | 25 | 90 | 0 | 100 | 95 | 0 | 100 | 100 | 100 | — |
| 115. | 25 | 100 | 0 | 100 | 100 | 0 | 100 | 100 | 100 | 100 |
| 116. | 25 | 100 | 0 | 100 | 100 | 0 | 100 | 100 | 100 | 100 |
| 117. | 25 | 95 | 0 | 100 | 100 | 0 | 95 | 100 | 95 | 100 |
| 118. | 25 | 100 | 0 | 100 | 100 | 0 | 100 | 100 | 95 | 75 |
| 119. | 25 | 100 | 0 | 100 | 100 | 95 | 100 | 100 | 100 | 100 |
| 120. | 25 | 100 | 0 | 100 | 100 | 0 | 100 | 100 | 100 | 100 |

"—" means Not Tested

The compounds of this invention were tested for fungicidal activity in vivo against cucumber downy mildew (CDM), rice blast (RB), tomato late blight (TLB), wheat powdery mildew (WPM), wheat leaf blotch (SNW) and wheat leaf rust (WLR). The compounds were dissolved in a 2:1:1 mixture of water, acetone, and methanol, sprayed onto the plants, allowed to dry (24 to 30 hours), and then the plants were inoculated with the fungus. Each test utilized control plants which were sprayed with the water, acetone and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

CUCUMBER DOWNY MILDEW (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

RICE BLAST (RB)

M-201 rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

TOMATO LATE BLIGHT (TLB)

*Phytophthora infestans* was cultured on V-8 Juice agar plates in an incubator at 18° C. in the dark. After growth, the spores were washed from the agar plates with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room (65° F.-70° F. and 80-90 relative humidity). Disease control levels were recorded as percent control 3-5 days after inoculation.

WHEAT POWDERY MILDEW (WPM)

*Erysiphe graminis* (f. sp. tritici) was cultured on Fielder wheat seedlings in a controlled temperature room at 65° F. to 75° F. Mildew spores were shaken from the culture plants onto Fielder wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

WHEAT LEAF BLOTCH (SNW)

*Septoria nodorum* was maintained on Czapek-Dox V-8 plates in an incubator in the dark at 20° C. for 48-72 hours, then incubated at 20° C. with alternating light and dark (12 hours:12 hours). A water suspension of the spores, obtained from the plates by shaking the portion of the plate with fungal material in deionized water and filtering through cheesecloth, was diluted to a spore concentration of $3.0 \times 10^6$ per milliliter.

The inoculum was dispersed by DeVilbiss atomizer over one week old Fielder wheat plants which had been sprayed previously with experimental fungicides. The inoculated plants were placed in a humidity cabinet at 20° C. with 12 hour:12 hours light/dark for 96 hours. The inoculated seedlings were then moved to the controlled environment room as above and scored after 8 more days incubation. Disease control levels were recorded as percent control ten days after inoculation.

WHEAT LEAF RUST (WLR)

*Puccinia recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

The results are shown in Table V.

TABLE V

| Green House Test Results of Plant diseases Control | | | | | | | |
|---|---|---|---|---|---|---|---|
| Com- | Rate | % Control | | | | | |
| pound | (ppm) | CDM | RB | SNW | TLB | WLR | WPM |
| 1. | 200 | 0 | —* | — | 50 | 0 | 0 |
| 2. | 200 | 0 | 50 | 0 | 0 | 0 | 0 |
| 3. | 200 | 90 | — | — | 50 | 90 | 0 |
| 4. | 600 | 100 | — | — | 0 | 64 | — |
| 5. | 600 | 100 | — | — | 0 | 13 | — |
| 6. | — | — | — | — | — | — | — |
| 7. | 200 | 50 | — | — | 50 | 99 | 0 |
| 8. | 200 | 0 | 50 | 0 | 0 | 80 | 0 |
| 9. | 200 | 85 | — | — | 95 | 90 | 0 |
| 10. | 200 | 75 | — | — | 0 | 99 | 0 |
| 11. | 200 | 0 | 75 | 50 | 90 | 80 | 75 |
| 12. | 200 | 80 | 75 | 90 | 0 | 90 | 75 |
| 13. | 200 | 90 | 0 | 80 | 0 | 50 | 0 |
| 14. | 200 | 90 | — | — | 90 | 90 | 0 |
| 15. | 200 | 0 | 0 | 0 | 0 | 50 | 0 |
| 16. | 200 | 80 | 75 | 80 | 0 | 90 | 75 |
| 17. | 200 | 90 | 90 | 90 | 0 | 80 | 75 |
| 18. | 200 | 70 | 0 | 80 | 0 | 50 | 85 |
| 19. | 200 | 50 | 0 | 80 | 0 | 50 | 50 |
| 20. | 200 | 50 | 90 | 80 | 0 | 80 | 75 |
| 21. | 200 | 0 | 0 | 0 | 0 | 50 | 0 |
| 22. | 200 | 0 | 0 | 0 | 0 | 0 | 0 |
| 23. | 200 | 0 | 0 | 0 | 0 | 0 | 0 |
| 24. | 200 | 0 | 0 | 0 | 0 | 50 | 0 |
| 25. | 600 | 83 | — | — | 49 | 76 | — |
| 26. | 600 | 97 | — | — | 47 | 71 | — |
| 27. | 200 | 80 | — | — | 0 | 0 | 0 |
| 28. | 600 | 90 | — | — | 29 | 78 | — |
| 29. | 200 | 90 | — | — | 0 | 95 | 0 |
| 30. | 200 | 90 | — | — | 0 | 85 | 85 |
| 31. | 200 | 0 | — | — | 50 | 75 | 0 |
| 32. | 600 | 90 | — | — | 4 | 60 | — |
| 33. | 200 | 0 | — | — | 0 | 95 | 0 |
| 34. | 200 | 50 | 90 | 80 | 50 | 0 | 0 |

TABLE V-continued

| Green House Test Results of Plant diseases Control | | | | | | | |
|---|---|---|---|---|---|---|---|
| Com- | Rate | % Control | | | | | |
| pound | (ppm) | CDM | RB | SNW | TLB | WLR | WPM |
| 35. | 200 | — | 75 | 50 | 0 | 80 | 0 |
| 36. | 200 | 85 | — | 0 | 0 | 0 | 0 |
| 37. | 200 | 0 | — | — | 0 | 0 | 0 |
| 38. | 300 | 96 | — | 71 | 0 | 66 | — |
| 39. | 200 | — | — | 50 | 75 | 90 | 0 |
| 40. | 300 | 91 | — | 74 | 20 | 82 | — |
| 41. | 300 | 96 | — | 87 | 32 | 90 | — |
| 42. | 300 | 92 | — | 63 | 19 | 81 | |
| 43. | 200 | 0 | — | 0 | 0 | 50 | 0 |
| 44. | 300 | 93 | — | 86 | 91 | 86 | — |
| 45. | 300 | 88 | — | 60 | 39 | 88 | — |
| 46. | 200 | 0 | — | — | 0 | 75 | 0 |
| 47. | 200 | 90 | — | — | 90 | 95 | 0 |
| 48. | 300 | 98 | — | 68 | 44 | 97 | — |
| 49. | 200 | 0 | — | 80 | 85 | 50 | 0 |
| 50. | 200 | — | — | 50 | 75 | 80 | 0 |
| 51. | 300 | 58 | — | 70 | 50 | 97 | — |
| 52. | 300 | 98 | — | 70 | 50 | 93 | — |
| 53. | 200 | 90 | — | — | 0 | 99 | 0 |
| 54. | 300 | 98 | — | 70 | 67 | 91 | — |
| 55. | 300 | 100 | — | 77 | 58 | 88 | — |
| 56. | 300 | 100 | — | 60 | 67 | 91 | — |
| 57. | 200 | 0 | — | — | 0 | 50 | 0 |
| 58. | 300 | 80 | — | 26 | 0 | 88 | — |
| 59. | 300 | 93 | — | 82 | 53 | 91 | — |
| 60. | 300 | 42 | — | 86 | 72 | 86 | — |
| 61. | 300 | 99 | — | 77 | 53 | 86 | — |
| 62. | 300 | 42 | — | 60 | 39 | 91 | — |
| 63. | 200 | 100 | — | — | 75 | 90 | 0 |
| 64. | 300 | 100 | — | 86 | 53 | 88 | — |
| 66. | 200 | 0 | — | — | 0 | 75 | 0 |
| 67. | 200 | 70 | — | — | — | 95 | 0 |
| 68. | 200 | 100 | — | — | 0 | 90 | 0 |
| 69. | 200 | 0 | — | 50 | — | 80 | 0 |
| 70. | 200 | 50 | — | 50 | — | 50 | 90 |
| 71. | 300 | 25 | — | 44 | 50 | 86 | — |
| 72. | 200 | 90 | — | — | 0 | 0 | 0 |
| 73. | 200 | 95 | — | — | 0 | 75 | 0 |
| 74. | 200 | 0 | — | 0 | 85 | 50 | 0 |
| 77. | — | — | — | — | — | — | — |
| 78. | 300 | 96 | — | 74 | 53 | 88 | — |
| 79. | 300 | 93 | — | 65 | 64 | 86 | — |
| 80. | 200 | 50 | — | — | 0 | 0 | 0 |
| 81. | 200 | 75 | — | — | 75 | 85 | 0 |
| 82. | 200 | 50 | — | — | 75 | 75 | 0 |
| 83. | 200 | 95 | — | 0 | 70 | 90 | 90 |
| 84. | 200 | 85 | — | — | 75 | 95 | 0 |
| 85. | 200 | 75 | — | — | 85 | 75 | 0 |
| 86. | 300 | 100 | — | 44 | 67 | 93 | — |
| 87. | 200 | 80 | 0 | 50 | 80 | 50 | 0 |
| 88. | 200 | 70 | — | 80 | 85 | 80 | 100 |
| 89. | 200 | 50 | 90 | 50 | 85 | 80 | 75 |
| 90. | 200 | 0 | — | 50 | 0 | 80 | 50 |
| 91. | 200 | 80 | 0 | 0 | 85 | 80 | 0 |
| 92. | 200 | 0 | — | 0 | 0 | 80 | 0 |
| 93. | 200 | 0 | 0 | 50 | 90 | 80 | 0 |
| 94. | 200 | 70 | — | 50 | 85 | 95 | 0 |
| 95. | 200 | 0 | — | 80 | 0 | 80 | 85 |
| 96. | 200 | 70 | — | 50 | 85 | 95 | 0 |
| 97. | 200 | 0 | — | 0 | 0 | 80 | 0 |
| 98. | 200 | 90 | 75 | 50 | 70 | 80 | 75 |
| 99. | 200 | 70 | — | — | 0 | 50 | 0 |
| 100. | 200 | 0 | 50 | 0 | 0 | 25 | 75 |
| 101. | 200 | 70 | 0 | 0 | 0 | 0 | 0 |
| 102. | 200 | 70 | — | 50 | 0 | 80 | 0 |
| 103. | 200 | 0 | 50 | 0 | 0 | 25 | 75 |
| 104. | 200 | 0 | — | 0 | 90 | 50 | 0 |
| 105. | 200 | 95 | 0 | 0 | 80 | 80 | 75 |
| 106. | 200 | 0 | 0 | 0 | 95 | 0 | 50 |
| 107. | 200 | 90 | 90 | 80 | 95 | 80 | 0 |
| 108. | 200 | 75 | 0 | 0 | 80 | 90 | 0 |
| 109. | 200 | 50 | 0 | 0 | 80 | 50 | 90 |
| 110. | 200 | 0 | 0 | 0 | 70 | 50 | 85 |
| 111. | 200 | 70 | — | 0 | 0 | 50 | 0 |
| 112. | 200 | 50 | 50 | 50 | 0 | 50 | 0 |
| 113. | 200 | 90 | 99 | 80 | 80 | 80 | 85 |
| 114. | 200 | 70 | 0 | 0 | 0 | 0 | 0 |
| 115. | 200 | 50 | 75 | 0 | 70 | 50 | 75 |

TABLE V-continued

| | | Green House Test Results of Plant diseases Control | | | | | |
|---|---|---|---|---|---|---|---|
| Com-<br>pound | Rate<br>(ppm) | % Control | | | | | |
| | | CDM | RB | SNW | TLB | WLR | WPM |
| 116. | 200 | 0 | 0 | 50 | 90 | 80 | 0 |
| 117. | 200 | 70 | 75 | 0 | 80 | 80 | 0 |
| 118. | 200 | 90 | 0 | 50 | 80 | 80 | 90 |
| 119. | 200 | 70 | 0 | 50 | 95 | 80 | 85 |
| 120. | 200 | 0 | 0 | 0 | 70 | 50 | 85 |

*"—" means Not Tested

It is to be understood that changes and variations may be made without departing from the spirit and scope of the invention as defined by the appended claims.

What is claimed is:

1. A method of controlling fungus on agricultural crops which comprises treating the agricultural crop with a fungicidally effective amount of a compound having the formula

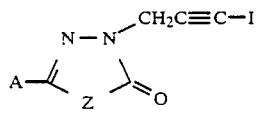

wherein
A is hydrogen, $(C_1-C_{18})$alkyl, $(C_3-C_8)$cycloalkyl, $(C_3-C_6)$alkenyl, $(C_3-C_6)$alkynyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, phenyl($C_1-C_6$)alkyl, naphthyl, thienyl, furyl or pyridyl; and
Z is oxygen or N-R;
wherein R is hydrogen, $(C_1-C_{12})$alkyl, $(C_3-C_6)$cycloalkyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, or phenyl$(C_1-C_6)$alkyl.

2. The method of claim 1 wherein the compounds have the formula

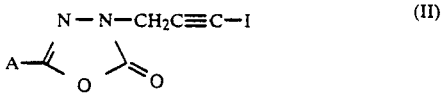

wherein A is $(C_1-C_{18})$alkyl, $(C_3-C_8)$cycloalkyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, phenyl($C_1-C_6$)alkyl, naphthyl, thienyl, furyl or pyridyl.

3. The method of claim 2 wherein A is phenyl, halophenyl, $(C_1-C_4)$alkylphenyl, nitrophenyl, halo$(C_1-C_4)$alkylphenyl or di$(C_1-C_4)$alkoxyphenyl.

4. The method of claim 3 wherein A is phenyl, fluorophenyl, chlorophenyl, methylphenyl, nitrophenyl, trifluoromethylphenyl or dimethoxyphenyl.

5. The method of claim 4 wherein A is phenyl, 2-fluorophenyl, 2-chlorophenyl, 3-chlorophenyl, 4-chlorophenyl, 2-methylphenyl, 3-methylphenyl, 2-nitrophenyl, 4-trifluoromethylphenyl or 2,5-dimethoxyphenyl.

6. The method of claim 1 wherein the compound has the formula

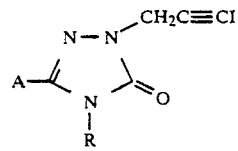

wherein A is hydrogen or $(C_1-C_4)$alkyl and R is phenyl optionally substituted by one to three substituents selected from halo, $(C_1-C_4)$alkyl, $(C_1-C_4)$alkoxy or nitro.

7. The method of claim 6 wherein A is hydrogen or t-butyl and R phenyl optionally substituted by one to three substituents selected from halo, $(C_1-C_4)$alkyl, $(C_1-C_4)$alkoxy or nitro.

8. The method of claim 7 wherein R is phenyl, fluorophenyl, chlorophenyl, methylphenyl, ethylphenyl, nitrophenyl, dichlorophenyl or dimethylphenyl.

9. The method of claim 8 wherein A is hydrogen and R is 2-fluorophenyl, 3-chlorophenyl, 2-methylphenyl, 3-methylphenyl, 4-methylphenyl, 3-ethylphenyl, 4-ethylphenyl, 2,4-dichlorophenyl, 3,5-dichlorophenyl, 3,5-dimethylphenyl or 2,4-dimethylphenyl.

10. The method of claim 8 wherein A is t-butyl and R is phenyl.

11. The method of claim 1 wherein the compound has the formula

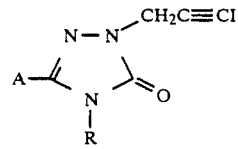

wherein A is hydrogen, $(C_1-C_4)$alkyl or phenyl optionally substituted by halo or $(C_1-C_4)$alkyl and R is $(C_1-C_{16})$alkyl or $(C_3-C_6)$cycloalkyl.

12. The method of claim 11 wherein A is hydrogen and R is $(C_3-C_6)$cycloalkyl.

13. The method of claim 11 wherein A is $(C_1-C_4)$alkyl and R is $(C_1-C_4)$alkyl or $(C_3-C_6)$cycloalkyl.

14. The method of claim 11 wherein A is fluorophenyl, chlorophenyl or methylphenyl and R is $(C_1-C_4)$alkyl.

15. The method of claim 12 wherein A is hydrogen and R is cyclohexyl.

16. The method of claim 13 wherein A is methyl and R is n-hexyl or cyclohexyl.

17. The method of claim 14 wherein A is 2-fluorophenyl, 3-fluorophenyl, 4-fluorophenyl, 2-chlorophenyl, 4-chlorophenyl, 2-methylphenyl or 4-methylphenyl and R is ethyl.

18. The method of claim 1 wherein the compound is administered in combination with another fungicidally effective compound.

19. A fungicidal composition which comprises an agriculturally acceptable carrier and a fungicidally effective amount of a compound of the formula

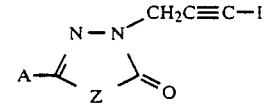

wherein

A is hydrogen, $(C_1-C_{18})$alkyl, $(C_3-C_8)$cycloalkyl, $(C_3-C_6)$alkenyl, $(C_3-C_6)$alkynyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, phenyl$(C_1-C_6)$alkyl, naphthyl, thienyl, furyl or pyridyl; and Z is oxygen or N-R;

wherein R is hydrogen, $(C_1-C_{12})$alkyl, $(C_3-C_6)$cycloalkyl, phenyl optionally substituted with one to three substituents selected from halo, nitro, $(C_1-C_6)$alkyl, halo$(C_1-C_6)$alkyl, halo $(C_1-C_4)$alkoxy and $(C_1-C_6)$alkoxy, or phenyl$(C_1-C_6)$alkyl.

20. The composition of claim 19 wherein the compound has the formula

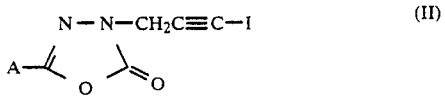

(II)

wherein A is $(C_1-C_{18})$alkyl, $(C_3-C_8)$cycloalkyl, phenyl optionally substituted with one to three substituents selected from halo, nitro, $(C_1-C_6)$alkyl, halo$(C_1-C_6)$alkyl, halo$(C_1-C_4)$alkoxy and $(C_1-C_6)$alkoxy, phenyl$(C_1-C_6)$alkyl, naphthyl, thienyl, furyl or pyridyl.

21. The composition of claim 20 wherein A is phenyl, halophenyl, $(C_1-C_4)$alkylphenyl, nitrophenyl, halo$(C_1-C_4)$alkylphenyl or di$(C_1-C_4)$alkoxyphenyl.

22. The composition of claim 21 wherein A is phenyl, fluorophenyl, chlorophenyl, methylphenyl, nitrophenyl, trifluoromethylphenyl or dimethoxyphenyl.

23. The composition of claim 22 wherein A is phenyl, 2-fluorophenyl, 2-chlorophenyl, 3-chlorophenyl, 4-chlorophenyl, 2-methylphenyl, 3-methylphenyl, 2-nitrophenyl, 4-trifluoromethylphenyl or 2,5-dimethoxyphenyl.

24. The composition of claim 19 wherein the compound has the formula

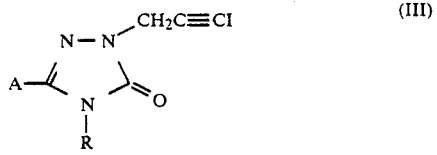

(III)

wherein A is hydrogen or $(C_1-C_4)$alkyl and R is phenyl optionally substituted by one to three substituents selected from halo, $(C_1-C_4)$alkyl, $(C_1-C_4)$alkoxy or nitro.

25. The composition of claim 24 wherein A is hydrogen or t-butyl and R phenyl optionally substituted by one to three substituents selected from halo, $(C_1-C_4)$alkyl, $(C_1-C_4)$alkoxy or nitro.

26. The composition of claim 25 wherein R is phenyl, fluorophenyl, chlorophenyl, methylphenyl, ethylphenyl, nitrophenyl, dichlorophenyl or dimethylphenyl.

27. The composition of claim 26 wherein A is hydrogen and R is 2-fluorophenyl, 3-chlorophenyl, 2-methylphenyl, 3-methylphenyl, 4-methylphenyl, 3-ethylphenyl, 4-ethylphenyl, 2,4-dichlorophenyl, 3,5-dichlorophenyl, 3,5-dimethylphenyl or 2,4-dimethylphenyl.

28. The composition of claim 27 wherein A is t-butyl and R is phenyl.

29. The composition of claim 19 wherein the compound has the formula

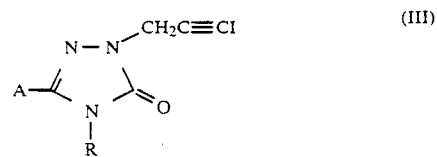

(III)

wherein A is hydrogen, $(C_1-C_4)$alkyl or phenyl optionally substituted by halo or $(C_1-C_4)$alkyl and R is $(C_1-C_{16})$alkyl or $(C_3-C_6)$cycloalkyl.

30. The composition of claim 29 wherein A is hydrogen and R is $(C_3-C_6)$cycloalkyl.

31. The composition of claim 29 wherein A is $(C_1-C_4)$alkyl and R is $(C_1-C_4)$alkyl or $(C_3-C_6)$cycloalkyl.

32. The composition of claim 29 wherein A is fluorophenyl, chlorophenyl or methylphenyl and R is $(C_1-C_4)$alkyl.

33. The composition of claim 30 wherein A is hydrogen and R is cyclohexyl.

34. The composition of claim 31 wherein A is methyl and R is n-hexyl or cyclohexyl.

35. The composition of claim 32 wherein A is 2-fluorophenyl, 3-fluorophenyl, 4-fluorophenyl, 2-chlorophenyl, 4-chlorophenyl, 2-methylphenyl or 4-methylphenyl and R is ethyl.

36. The composition of claim 19 wherein the compound is present in combination with another fungicidally effective compound.

* * * * *

UNITED STATES PATENT AND TRADEMARK OFFICE
CERTIFICATE OF CORRECTION

PATENT NO. : 5,064,845

DATED : November 12, 1991

INVENTOR(S) : Adam C. Hsu, Daniel L. Loughner

It is certified that error appears in the above-identified patent and that said Letters Patent is hereby corrected as shown below:

In the abstract, at column 1, lines 25-30 and at column 1, lines 55-60,

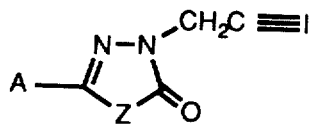   should read   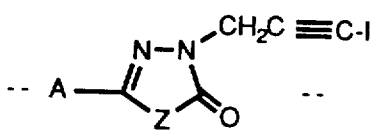

At column 3, line 40 "2-flourophenyl" should read "2-fluorophenyl".

Signed and Sealed this

Twenty-seventh Day of April, 1993

Attest:

MICHAEL K. KIRK

Attesting Officer

Acting Commissioner of Patents and Trademarks